United States Patent
Meinhold

(10) Patent No.: US 10,667,843 B2
(45) Date of Patent: Jun. 2, 2020

(54) GRIPPER HEAD FOR GRABBING A TICK AND A TICK GRIPPER

(71) Applicant: Matthias Meinhold, Nürnberg (DE)

(72) Inventor: Matthias Meinhold, Nürnberg (DE)

( * ) Notice: Subject to any disclaimer, the term of this patent is extended or adjusted under 35 U.S.C. 154(b) by 3 days.

(21) Appl. No.: 15/500,132

(22) PCT Filed: Jul. 29, 2015

(86) PCT No.: PCT/DE2015/000374
§ 371 (c)(1),
(2) Date: Jan. 30, 2017

(87) PCT Pub. No.: WO2016/015702
PCT Pub. Date: Feb. 4, 2016

(65) Prior Publication Data
US 2017/0245892 A1  Aug. 31, 2017

(30) Foreign Application Priority Data
Jul. 30, 2014 (DE) .................... 20 2014 006 075 U

(51) Int. Cl.
*A61B 17/50* (2006.01)
(52) U.S. Cl.
CPC ........ *A61B 17/50* (2013.01); *A61B 2017/505* (2013.01)
(58) Field of Classification Search
CPC ... A61B 17/50; A61B 2017/505; A61B 10/06; A61B 17/29; A61B 17/2909
See application file for complete search history.

(56) References Cited

U.S. PATENT DOCUMENTS

| 4,763,668 A | * | 8/1988 | Macek | A61B 10/06 600/564 |
| 5,172,700 A | * | 12/1992 | Bencini | A61B 10/06 600/564 |
| 6,139,508 A | * | 10/2000 | Simpson | A61B 10/06 600/564 |
| 2002/0095177 A1 | * | 7/2002 | Kupferschmid | A61B 17/29 606/205 |
| 2005/0119524 A1 | * | 6/2005 | Sekine | A61B 1/00135 600/114 |

OTHER PUBLICATIONS

Orkin as accessed Mar. 8, 2019; https://www.orkin.com/other/ticks/deer-ticks.*

* cited by examiner

*Primary Examiner* — Wade Miles
(74) *Attorney, Agent, or Firm* — Nancy J. Flint, Attorney at Law, P.A.; Nancy J. Flint, Esq.

(57) ABSTRACT

A gripper head for grabbing and fixing a tick comprises two facing gripping jaws, wherein the gripper head can adopt a state with open gripping jaws and a state with closed gripping jaws. The gripper head further comprises a holder comprising a closing spring for holding the two gripping jaws, wherein the gripping jaws are configured such that each of them has a curved outer side and a flat inner side, the closing spring acts on the two gripping jaws, and in the closed state of the gripping jaws the flat inner sides of the two gripping jaws lie on each other such that a closed body is formed. The gripper head is design to be accommodated and fastened to a tick gripper.

5 Claims, 4 Drawing Sheets

GRIPPER HEAD FOR GRABBING A TICK AND A TICK GRIPPER

Figure 1:
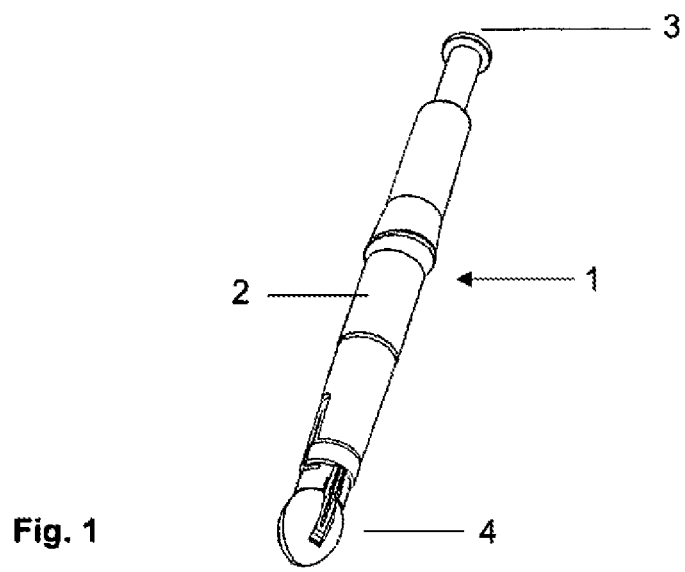

The invention relates to a gripper head for grabbing a tick, and to a tick gripper having such a gripper head.

Diseases transmitted from ticks to humans and animals are spreading wider and wider, wherein various diseases can be transmitted, depending on the infection of the tick. Borreliosis is in Germany the most frequent disease transmitted by ticks, with an estimated 60,000-100,000 new cases per annum, wherein in Germany up to 30% of ticks contain borreliae. In Germany alone, around 250 persons per annum contract early summer meningoencephalitis (ESME), around 30 percent thereof seriously. Ten percent of the diseased patients exhibit permanent, sometimes very serious neurological damage. Two percent of patients die of it.

The increase in tick-transmitted illnesses is worrying. According to estimates, 80 percent of all infections are the result of an improper removal of the tick. The timely and proper removal of the tick is prevention and treatment at the same time and can help to reduce the number of new cases in humans and animals. By proper removal is understood the removal of the undamaged tick without it being squeezed or otherwise irritated, and without an infection being thereby initiated.

Traditionally, ticks are removed with forceps, a card, a loop, tweezers, or with the finger nails. Yet care should be taken to in no event squeeze the tick, for in the salivary glands and gastro-intestinal tract can be found pathogens, which, upon the slightest application of pressure, are transmitted to the human. Rigid materials, which inevitably squeeze the body of the tick and thus substantially increase the risk of disease, are therefore to be avoided.

Recent scientific studies show that, when all criteria are considered, preference can be given to the tools which remove the ticks by means of rotation, compared to those which remove the ticks by traction. See Klaus Robisch: "Tick Removal—Vergleich von fünf verschiedenen Zeckenentfernungsgeräten" (Comparison of Five Different Tick-Removing Tools), thesis for acquiring the title of "Diplomtierarzt" (≈ Bachelor of Science in Veterinary Medicine) of the University of Veterinary Medicine in Vienna, November 2010 (http://www.zeckenzange.eu/Zeckenentfernung.pdf).

Printed publication DE 10 2004 031 682 A1 discloses an apparatus for removing ticks or similar parasites from the skin of animals or humans, which is also referred to as a tick gripper. The apparatus here has a housing, an expandable gripper head, an expansion device for expanding the gripper head, and a rotation device for rotating the gripper head about the longitudinal axis of the apparatus, wherein the gripper head, in its unexpanded state, encloses a substantially closed hollow space for receiving the parasite or tick. Furthermore, the apparatus or tick gripper has a pressure device which acts in the axial direction and by means of which the expansion and rotation of the gripper head is effected.

In the known tick gripper, a "slackening" of the gripper head can ensue after continued actuation, so that an exact closure of the gripping jaws is not necessarily guaranteed.

The object of the invention is therefore to improve the gripper head of a tick gripper, and thus the tick gripper itself.

This object is achieved by a gripper head for a tick gripper, as well as by a corresponding tick gripper.

The gripper head according to the invention for grabbing and fixing a tick comprises two mutually facing gripping jaws, wherein the gripper head can adopt a state with open gripping jaws and a state with closed gripping jaws. In addition, the gripper head comprises a holder having a closing spring for receiving the two gripping jaws, wherein the gripping jaws are configured such that they respectively have a curved outer side and a flat inner side, the closing spring acts on the two gripping jaws, and, in the closed state of the gripper head, the flat inner sides of the two gripping jaws lie one upon the other, so that a closed body is formed.

Preferably, the two gripping jaws respectively have an inner cavity. By the two cavities of the two gripping jaws is formed, in the closed state of the gripper head, an inner hollow space, which receives parts of the tick body, whereby a pressure on the body of the tick is avoided and the tick is fixed only by its head part, by means of the pointed front part of the body formed by the gripping jaws, wherein the closed body has roughly the shape of a forward tapered ellipsoid of revolution.

Further preferredly, the closing spring has two mutually facing spring elements. In addition, each gripping jaw has on its outer side a recess, so that the spring elements can engage in the recesses of the gripping jaws.

Further preferredly, the spring elements of the closing spring have a predefined preload, whereby the closure of the gripping jaws in the closed state of the gripper head is effected. The spring constant of the closing spring is here chosen such that no excessive squeezing of the tick to be removed takes place.

Preferably, the gripping jaws consist of a thermoplastic elastomer (TPE). TPE is regarded as an alternative material to silicone and boasts excellent mechanical properties, for it is extremely flexible, has a smooth surface, is UV-resistant and weather-resistant, possesses good resilience and is usable within a wide operating temperature range from $-40°$ C. to $+120°$ C.

Further preferredly, the holder of the gripper head has a device for detachably fixing the gripper head to a tick gripper. This can be realized, for instance, by a suitable plug and socket connection, by means of which the gripper head can be fixedly but detachably plugged onto the tick gripper.

The tick gripper according to the invention for grabbing and fixing a tick comprises an elongate main body, a pressing/rotating device disposed in the main body, and a gripper head for grabbing and fixing the ticks, wherein the gripper head is set in rotation by the pressing/rotating device, protruding at one end from the main body, and can be opened and closed. A gripper head described in the above is here employed in the tick gripper.

Preferably, the pressing/rotating device of the tick gripper is configured at one end of the main body as a pressure pin and has at the other end a receiving fixture for the detachable fastening and fixing of the gripper head.

Further preferredly, with the retraction of the pressure pin of the pressing/rotating device into the main body, the gripper head is firstly set in rotation, shortly before reaching of the completely retracted position, the rotation is ended and the gripper head opened, with the extension of the pressure pin from the main body, the gripper head is closed again and, upon a further extension of the pressure pin from the main body, the gripper head is set in rotation until the fully extended state of the pressure pin is reached.

Figure 2:
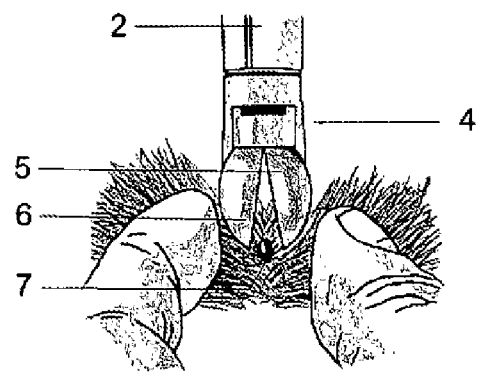
Figure 3:
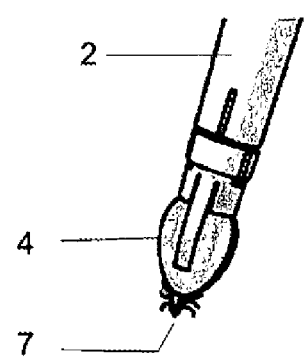
Figure 4:
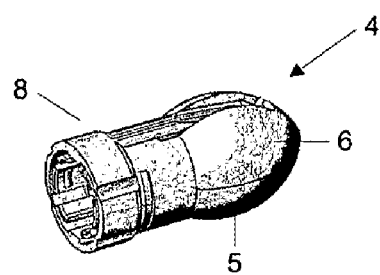
Figure 5:
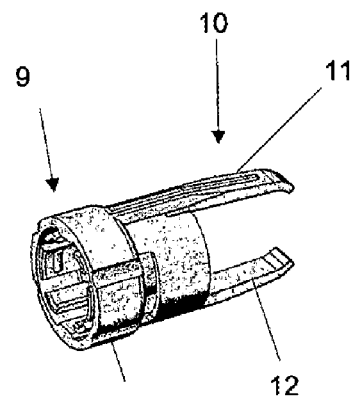
Figure 6:
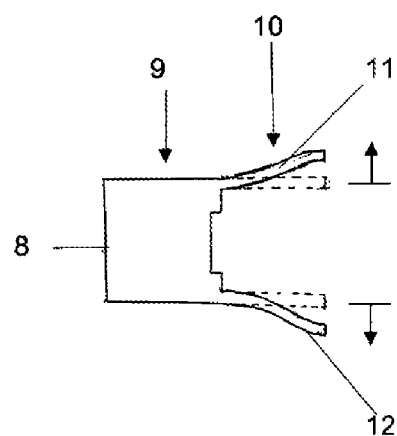
Figure 7:
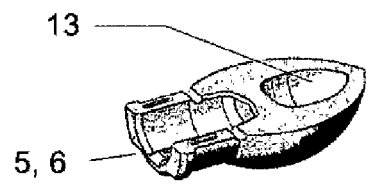
Figure 8:
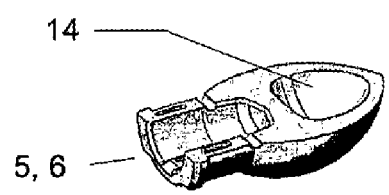

A preferred embodiment of the invention is explained in greater detail below with reference to the drawings, wherein:

FIG. 1 shows a tick gripper with gripper head,
FIG. 2 shows the open gripper head in one application,
FIG. 3 shows the closed gripper head with a tick,
FIG. 4 shows the gripper head in detail,
FIG. 5 shows the holder of the gripper head with closing spring, FIG. 6 shows the closing spring in detail, FIG. 7 shows a gripping jaw of the gripper head with small cavity, and FIG. 8 shows a gripping jaw of the gripper head with large cavity.

FIG. 1 shows a tick gripper 1 in perspective view. The tick gripper 1 here comprises a main body 2, in which is movably arranged a pressing/rotating device 3, which acts on a gripper head 4. The gripper head 4, which is disposed on the main body 2 of the tick gripper 1, here serves to grab a parasite, in particular a tick, wherein the gripper head 4 is fixedly but detachably connected to the pressing/rotating device 3, for instance by means of a latching device.

The concept on which the tick gripper 1 is based is described in the above-stated DE 10 2004 031 682 A1. Through an axial pressure, for instance by the thumb of one hand, onto the pressing/rotating device 3 in the direction of the main body 2, a rotation of the gripper head 4 is firstly effected. Shortly before reaching of the fully retracted position of the pressing/rotating device 3 into the main body 2, the rotation of the gripper head is ended and an opening of the gripper head takes place until, with the fully retracted pressing/rotating device 3, a maximum opening of the gripper head 4 is realized. An abatement of the pressure on the pressing/rotating device 3 produces a closure of the gripper head 4, wherein a further abatement of the pressure after the closure of the gripper head 4 produces a rotation of the same until the pressing/rotating device 3 is back in the starting position. In other words, the pressing of the pressing/rotating device 3 into the main body 2 firstly produces a rotation of the gripper head 4 with subsequent opening of the same, while the withdrawal of the pressing/rotating device 3 from the main body 2 through abatement of the pressure firstly produces a closure of the gripper head 4 with a following rotation of the gripper head 4.

FIG. 2 schematically describes the grasping of the tick 7 with the open gripper head 4, which in this representation has a left gripping jaw 5 and a right gripping jaw 6. In FIG. 2 is represented a tick 7, which has attached itself in the skin in the hair region of a human or of an animal. In order to be able to remove this tick 7, the tick 7 in the hair region is exposed by the finger of a person. The gripper head 4 is then placed with the open jaws 5, 6 over the tick 7, the tick gripper 1 here being represented schematically by a part of the main body 2. Once this is done, then the gripper head 4 is closed and the tick 7 is grabbed by the gripping jaws 5, 6 of the gripper head 4. The closure of the gripper head 4 is realized by abatement of the pressure on the pressing/rotating device 3, so that the pressing/rotating device moves back out of the main body 2. Once the closure of the gripper head 4 is ended and the tick is grabbed, then a further abatement of the pressure on the pressing/rotating device 3 produces a rotation of the gripper head 4, whereby the tick 7 is removed from the skin of the patient.

In FIG. 3, the end state after the removal of the tick 7 from the skin of the patient is represented schematically. Once the pressing/rotating device 3 is fully untensioned and has assumed the extended end position in the main body 2 of the tick gripper 1, the tick 7 is fixed in the gripping jaws of the gripper head 4, the tick gripper 1 being represented schematically in the figure by a part of the main body 2.

FIG. 4 shows in perspective representation the gripper head 4 of a tick gripper 1, which has a holder 8 in which the two gripping jaws 5, 6 are disposed. In the arrangement of FIG. 4, one of the gripping jaws 5, 6 is at the top and the other at the bottom.

In FIG. 5, the holder 8 is represented in greater detail and without the two gripping jaws 5, 6. The holder 8 here comprises a base 9, which serves for the fitting of the gripper head 4, by means of a suitable clamping device (not represented), onto the pressing/rotating device 3. In addition, adjoining the base 9 of the holder 8 is a closing spring 10, wherein the closing spring 10 has a first spring element 11 and a second spring element 12. The spring elements 11, 12 lie one opposite the other and are configured such that they respectively engage in a corresponding recess of the respective gripping jaw 5, 6, as can be seen from FIG. 4.

The properties of the closing spring 10 are influenced by various factors, such as, for instance, material selection, additions to the material, molding and tool design, processing or environmental conditions. Through specification of the necessary material constants and calculations for determining spring and joining forces in the opening and closure of the gripper head 4, an exact opening and closing behavior can be ensured. The closing behavior can be determined from the force curve which derives from the closing force of the gripper head 4 as a function of the opening width and is critical to ensuring that, though the tick is held, it is not excessively pressed. The opening behavior derives from the necessary pressure on the pressure head and from the maximum expansion width, which is reached after a 720° rotation. The preload at the moment of joining of the two components is 1.1 N per spring element 11, 12. By relaxation of tension, the preload is reduced over time, the long-term value for about 10 years amounting to 0.5 N per spring element 11, 12.

FIG. 6 shows the principle of the closing spring 10 in schematic representation. The spring elements 11, 12 of the closing spring 10 are designed in one piece with the base 9 of the holder 8. The spring elements 11, 12 are here movable out of the rest position (shown in dashed representation) outward in the direction of the arrows. In other words, in the untensioned state (shown in dashed representation), the spring elements 11, 12 press the gripping jaws (not represented) together. If the spring elements 11, 12 are pressed outward by the pressing/rotating device 3 (not represented), then the gripping jaws 4, 5 of the gripper head 4 open.

FIG. 7 shows in perspective top view a gripping jaw 5, 6, which is disposed in the holder 8 represented in FIG. 5. The represented gripping jaw 5, 6 here has a small cavity 13 with reinforced wall, for grasping of small and very small ticks.

FIG. 8 finally shows a further version of the gripping jaw 5, 6, having a large cavity 14 for receiving large ticks.

The shaping of the gripping jaws 5, 6 takes account of the morphology of the tick. Since ticks are often noticed on the human skin at an early stage, smaller ticks are here likely to have to be removed. In dense animal fur, ticks are normally discovered later, so that in animals larger ticks tend to have to be removed. In humans and animals, differently shaped gripping jaws having differently sized cavities 13, 14 are therefore employed. The aim is to keep the pressure on the salivary glands, in which the ESME virus can be found, or the pressure on the intestine, in which borreliae and other pathogenic bacteria can be found, as low as possible.

Small ticks, i.e. ticks <2 mm, for example nymphs or so-called "baby ticks", are enclosed in their entirety by the gripping jaws. They "disappear" in the wall thickness of the gripping tip. For this reason, the use of a soft material is important.

Medium-sized ticks, i.e. ticks of 2 mm to 4 mm, are grasped by the head and the proximal trunk, by means of the tip of the gripper head. The abdomen of the tick lies in the cavity. Large ticks, i.e. ticks >4 mm, are grasped, like the medium-size ticks, by the head and proximal trunk, by means of the tip of the gripper head, but the greatest part of the body lies in the cavity. The latter should be appropriately sized in order that the pressure on the intestine of the tick is small.

In other words, type 1 (represented in FIG. 7), with small cavity 13, is suitable for small ticks, while type of the gripper head 4 (represented in FIG. 8), with large cavity 14, is suitable for larger ticks.

In addition, the gripping jaws 5, 6 must be produced from a material which
- by virtue of its intrinsic elasticity, does not press too strongly on the tick, and
- by virtue of its surface characteristics, entails minimal friction losses in the transmission of the rotational force to the tick.

These material requirements are met by TPE (thermoplastic elastomer). TPE is regarded as an alternative material to silicone and boasts excellent mechanical properties, for it is extremely flexible, has a smooth surface, is UV-resistant and weather-resistant, possesses good resilience and is usable within a wide operating temperature range (−40° C. to +120° C.). TPE is dynamically loadable up to 100° C. In addition, TPE complies with the regulations of the FDA (Food and Drug Administration) and is recyclable. Different hardnesses are employed in the manufacture of the gripping jaws, for example 44, 55 and 65 Shore.

In summary, the gripping jaws of the gripping head 4 according to the invention, or of the tick gripper 1, meet the following requirements:
- the gripping body can be opened to the extent that even large ticks can be grasped,
- the gripping head can be exactly closed, that even nymphs of a size smaller than 1 mm are grasped,
- the tick is squeezed as little as possible,
- the gripping head rotates evenly in order for the ticks to be turned out, and
- the exact opening and closing behavior of the gripping head is maintained, even if this is very often successively opened and closed, or is not actuated for a long time, and is exposed to a temperature range from 5° to 50° Celsius.

In addition, the gripping jaws have an adhesive surface, so that the tick sticks to the surface. A killing of the tick 7 can be realized by means of electricity, heat, cold or chemical reactions following removal of the tick from the skin. Finally, the material of the gripping jaws can be transparent in order to improve the view of the object to be removed, wherein the fitting of a light source and/or magnifier to the tick gripper can be sensible, in particular in the case of small ticks.

REFERENCE SYMBOL LIST 1 tick gripper
2 main body
3 pressing/rotating device
4 gripper head
5 gripping jaw
6 gripping jaw
7 tick
8 holder
9 base
10 closing spring
11 spring element
12 spring element
13 small cavity
14 large cavity

The invention claimed is:

1. A tick gripper for grabbing, fixing, and removing a tick, comprising:
a gripper head including two gripping jaws, wherein the gripper head can adopt a state with open gripping jaws and a state with closed gripping jaws;
an elongate main body and a pressing/rotating device disposed in the main body; and
a holder disposed on one end of the main body, the holder for receiving two gripping jaws, wherein the holder comprises a base with an adjoining closing spring, wherein the gripping jaws are configured such that they respectively have a curved outer side and a flat inner side, wherein the closing spring acts on the two gripping jaws, wherein the closing spring has two mutually facing spring elements, wherein each gripping jaw has on its outer side a recess, wherein the spring elements engage in the recesses of the gripping jaws and, in the closed state of the gripper head, the flat inner sides of the two gripping jaws lie one upon the other, so that a closed body is formed,
wherein the closing spring comprises a spring constant with a predefined preload for closing the gripping jaws,
wherein further an axial pressure on the pressing/rotating device in the direction of the gripping jaws causes each of the spring elements to move out of a rest position where the spring elements are in an untensioned state which effectuates an opening of the gripping jaws,
wherein thereafter a release of the axial pressure on the pressing/rotating device causes each of the spring elements to move back to the rest position where the spring elements are in an untensioned state and effectuates a closing of the gripping jaws.

2. The tick gripper as claimed in claim 1, wherein the two gripping jaws respectively have an inner cavity.

3. The tick gripper as claimed in claim 2, wherein the spring elements of the closing spring have a predefined preload at the moment of joining of the two gripping jaws is 1.1 N per spring element, whereby the closure of the gripping jaws in the closed state of the gripper head is effected.

4. The tick gripper as claimed in claim 1, wherein the gripping jaws consist of a thermoplastic elastomer.

5. The gripper head tick gripper as claimed in claim 1, wherein the holder has a device for detachably fixing the gripper head to the main body.

* * * * *